United States Patent [19]
Kang et al.

[11] Patent Number: 6,035,230
[45] Date of Patent: Mar. 7, 2000

[54] REAL-TIME BIOLOGICAL SIGNAL MONITORING SYSTEM USING RADIO COMMUNICATION NETWORK

[75] Inventors: Dong-Joo Kang, Seoul; Dong-Wha Lee, Suwon, both of Rep. of Korea

[73] Assignee: Medison Co., Ltd, Rep. of Korea

[21] Appl. No.: 09/043,089

[22] PCT Filed: Sep. 11, 1996

[86] PCT No.: PCT/KR96/00156

§ 371 Date: Mar. 11, 1998

§ 102(e) Date: Mar. 11, 1998

[87] PCT Pub. No.: WO97/09923

PCT Pub. Date: Mar. 20, 1997

[30] Foreign Application Priority Data

Sep. 13, 1995 [KR] Rep. of Korea ................. 95-29913

[51] Int. Cl.[7] ............................................. A61B 5/021
[52] U.S. Cl. .............................................. 600/509
[58] Field of Search ........................... 128/903; 600/509

[56] References Cited

U.S. PATENT DOCUMENTS 4,958,645 9/1990 Cadell et al. .
5,462,051 10/1995 Oka et al. ............................... 128/903

FOREIGN PATENT DOCUMENTS

7/234982 9/1995 Japan .

*Primary Examiner*—Scott M. Getzow
*Attorney, Agent, or Firm*—Dilworth & Barrese

[57] ABSTRACT

A real-time biological signal monitoring system using a radio communication network includes a portable biological signal hold apparatus (100) attached to the body of a patient for measuring biological signal data, judging whether or not the measured biological signal data is normal, and transmitting abnormal biological signal data via an aerial radio communication network whenever it is judged as an abnormal state, and a biological signal monitoring server apparatus (300) for diagnosing the biological signal data for which an abnormality is recognized from the biological signal hold apparatus (100) via the aerial radio communication network and transmitting a resultant prescription message to the biological signal hold apparatus. The biological signal monitoring system provides an effect capable of monitoring and providing an emergency treatment on a real-time basis via a radio communication network. Also, an expensive storage unit is not used to record the biological signal data and an additional connection apparatus is not required to transmit data at high speed, resulting in providing a more economical apparatus compared with the conventional biological signal remote measuring apparatus.

13 Claims, 3 Drawing Sheets

REAL-TIME BIOLOGICAL SIGNAL MONITORING SYSTEM USING RADIO COMMUNICATION NETWORK

TECHNICAL FIELD

The present invention relates to a biological signal monitoring system, and more particularly, to a real-time biological signal monitoring system using a radio communication network in which biological signal data is checked using a portable biological signal hold apparatus, the checked data is transmitted to a monitoring center via an aerial radio communication network when it is judged as abnormality, and then the monitoring center transmits diagnosis and prescription information to the biological signal hold apparatus in response thereto.

BACKGROUND ART

A technique of measuring biological signals at a remote distance is recently under development according to the technological advancement of a medical science. A recent biological signal remote measuring method which is widely used is an electrocardiogram transmission method. There are monitors for a Holter electrocardiogram, a resting electrocardiogram and a stress electrocardiogram as electrocardiogram monitoring apparatuses used for diagnosing heart disease and the state of the heart.

Taking an electrocardiogram as an example, problems of conventional art will be briefly described below. Generally, an electrocardiograph can observe the waveforms of an electrocardiogram for a short time. However, the waveforms of an electrocardiogram should be continuously recorded for a long time and the recorded data should be analyzed to observe heart abnormality such as an irregular pulse which is generated intermittently. For this purpose, a Holter electrocardiogram apparatus has been developed. Recently, it is a tendency that the Holter electrocardiogram apparatus is put on for about one day to record detected electrocardiogram data on a cassette tape or a semiconductor storage unit for more than 24 hours and to analyze the recorded data. However, it takes much time to analyze the recorded data, and particularly much more time to analyze a more technological analysis.

For this reason, the heart disease of a patient does not measured in real-time. As a result, when a patient is in an emergency situation, an emergency treatment cannot be taken immediately. Also, since a terminal of the Holter electrocardiogram apparatus stores data corresponding to the quantity of more than 24 hours, an expensive storage unit such as a memory card is needed and a separate connection apparatus is needed to transmit the data at high speed. As a result, an equipment cost rises.

DISCLOSURE OF INVENTION

To solve the above problems, it is an object of the present invention to provide a real-time biological signal monitoring system using a radio communication network to enable diagnosis and prevention with respect to the disease of a patient in which a biological signal hold apparatus is put on by a patent and then an electrocardiogram or various kinds of biological signal data are continuously checked to transmit the checked data to a biological signal monitoring server apparatus in a hospital on a real-time basis via a radio communication network only when it is judged as an abnormality condition, within the boundary where an activity area of the patient is not limited, and a biological signal monitoring center of the hospital transmits diagnosis and prescription to the biological signal hold apparatus on a real-time basis.

To accomplish the above object of the present invention, there is provided a biological signal monitoring system using a radio communication network comprising:

a portable biological signal hold apparatus attached to the body of a patient for measuring biological signal data, judging whether or not the measured biological signal data indicates an abnormality, and transmitting the biological signal data indicating the abnormality via an aerial radio communication network whenever it is judged as an abnormal state;

a biological signal monitoring server apparatus for diagnosing the biological signal data with which an abnormality is recognized from the biological signal hold apparatus via the aerial radio communication network and transmitting a resultant prescription message to the biological signal hold apparatus; and a relay station for playing a role of relaying abnormal biological signal data transmitted from the biological signal hold apparatus to the biological signal monitoring server apparatus in a hospital.

BEST MODE FOR CARRYING OUT THE INVENTION

A preferred embodiment of the present invention will be described below with reference to the accompanying drawings.

Figure 1:
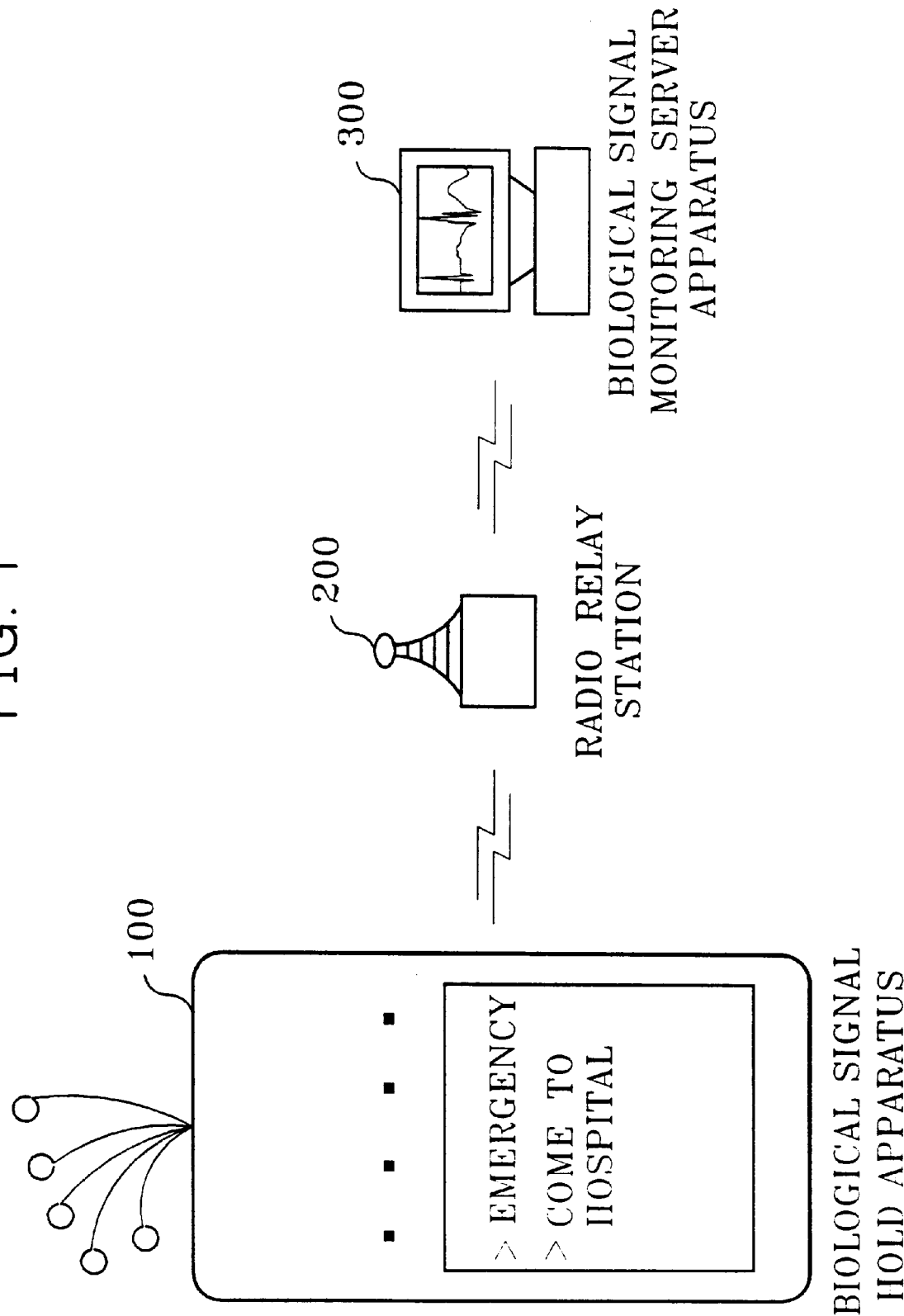
FIG. 1 is a schematic diagram showing a biological signal monitoring system including a portable biological signal hold apparatus, a biological signal monitoring server apparatus for monitoring biological signal data transmitted from the biological signal hold apparatus and a radio relay station installed between the biological signal hold apparatus and the biological signal monitoring server apparatus, according to a preferred embodiment of the present invention.

Referring to FIG. 1, a biological signal monitoring system according to a preferred embodiment of the present invention includes a portable biological signal hold apparatus 100, and a biological signal monitoring server apparatus 300 for monitoring biological signal data transmitted from the biological signal hold apparatus and a relay station 200 installed between the biological signal hold apparatus 100 and the biological signal monitoring server apparatus 300. The portable biological signal hold apparatus 100 checks biological signal data by attaching a plurality of electrodes to the body of a patient. The biological signal hold apparatus 100 is constructed so that biological signal data is continuously checked and the biological signal data indicating an abnormality is transmitted to a radio relay station 200 via an internal radio modem (not shown) only when there is an abnormal situation. The radio relay station 200 transfers the biological signal data supplied from the biological signal hold apparatus 100 to the biological signal monitoring server apparatus 300 in a hospital. The biological signal monitoring server apparatus 300 monitors the received biological signal data and transmits the treatment and emergency prescription corresponding to the biological signal data indicating an abnormality to the biological signal hold apparatus 100.

Figure 2:
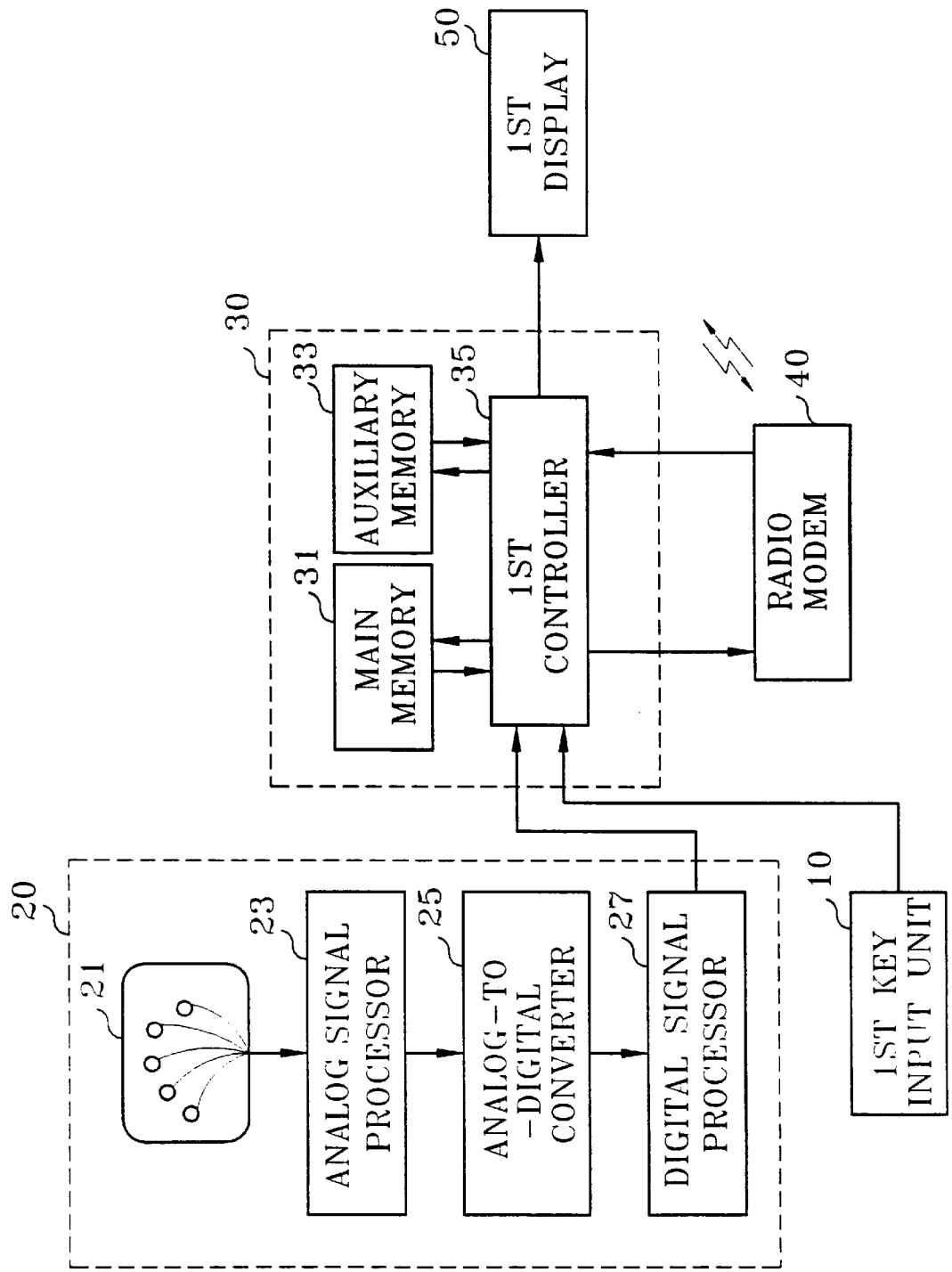
FIG. 2 is a block diagram showing the portable biological signal hold apparatus of FIG. 1.

FIG. 2 is a detailed block diagram showing the portable biological signal hold apparatus 100 attached to the body of a patient, for checking whether or not there is an abnormality in the body of the patient. The biological signal hold apparatus 100 includes a biological signal data measuring unit 20, attached to the body of the patient, for sensing a minute electrical signal generated during activity of each organ of the human body. The biological signal hold apparatus 100 also includes a first key input unit 10 for manually applying a signal indicating an abnormality to the biological signal monitoring server apparatus 300 in a hospital when a patient feels an abnormality in his or her body although the biological signal data measuring unit 20 does not measure the abnormality of the body. A biological signal analysis unit 30 is connected to receive biological signal data measured in the biological signal data measuring unit 20. The biological signal analysis unit 30 is constructed so that it receives a key signal which is manually input from the key input unit 10 by the patient and transmits the received key signal to the relay station 200 via a radio modem 40. A main memory 31 in the biological signal analysis unit 30 includes a ROM which stores a program for checking the occurrence of an abnormality of the patient and a RAM for temporarily storing the biological signal data between several minutes before or after the occurrence of the abnormality of the living body is checked. The biological signal data analysis unit 30 may also further include an auxiliary memory 33 for storing the biological signal data for a long time. Also, the biological signal hold apparatus 100 includes a display unit 50, so that it can display an emergency treatment, for example, a statement such as "Emergency, Come to the hospital" which is transmitted from the biological signal monitoring server apparatus 300 in the hospital.

Now, the biological signal hold apparatus 100 attached to the body of the patient to check the biological signal data will be described in more detail.

The biological signal data measuring unit 20 includes an electrode portion 21 having a predetermined number of electrodes 21 attached to the body of the patient to sense an electrical signal of the human body. In this embodiment, the electrode portion 21 has five electrodes one of which is grounded and the others of which are used for measuring the difference between electric potentials of each of two pairs of the electrodes. The two electric potential differences can be finally obtained in an analog signal processor 23. The biological signal data is converted into digital data in an analog-to-digital converter 25. A digital signal processor 27 processes the received digital biological signal data and outputs the processed result to a first controller 35 in the biological signal analysis unit 30. The first controller 35 checks whether or not the body of the patient is abnormal using the received biological signal data through execution of the program stored in the main memory 31. Here, the first controller 35 stores biological signal data which indicates that the body of the patient is in a normal condition and becomes a reference for judging the occurrence of the abnormality in the human body using the biological signal data. The first controller 35 checks the biological signal data which is successively input from the biological signal data measuring unit 20, compares the biological signal data with predetermined biological signal data indicating a normality, and then outputs a command, that is, a call control signal for connection to the biological signal monitoring server apparatus 300 in the hospital via the radio communication network, to the radio modem 35 if it is checked as the occurrence of an abnormality. Also, the first controller 35 temporarily stores the preceding or following data of the abnormality-checked biological signal data in the main memory 31 for several minutes. In this embodiment, the preceding or following data of the abnormality-checked biological signal data is stored in the main memory 31 for eight seconds. If the biological signal monitoring system is connected to the radio communication network, the data stored in the main memory 31 is transmitted to the hospital biological signal monitoring server apparatus 300 via the radio modem 40 and a radio relay station 200.

The biological signal monitoring server apparatus 300 in a hospital is connected to a communication control unit CCU (not shown) in the hospital, and is constituted so that the biological signal data transmitted from each biological signal hold apparatus 100 which is attached to each patient can be continuously monitored.

Figure 3:
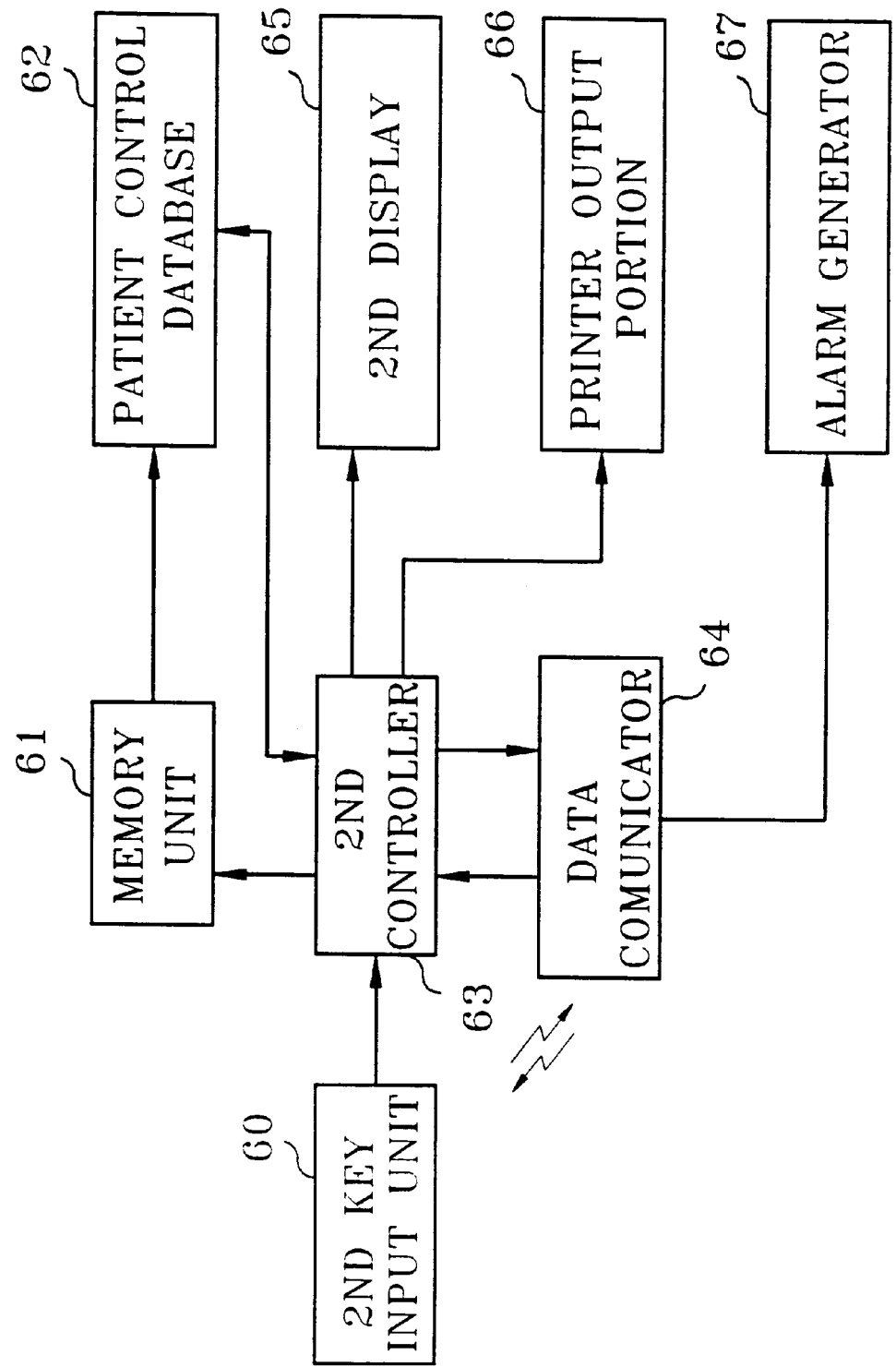
FIG. 3 is a block diagram showing the biological signal monitoring server apparatus of FIG. 1.

FIG. 3 is a block diagram showing the biological signal monitoring server apparatus 300 of FIG. 1, which is installed in a hospital. The biological signal monitoring server apparatus 300 includes a data communicator 64 for transmitting and receiving with respect to the biological signal hold apparatus 100. Moreover, the biological signal monitoring server apparatus 300 includes an alarm generator 67 for generating an alarm if the biological signal hold apparatus 100 is connected with the data communicator 64 via the radio communication network to enable data communication. Also, the biological signal monitoring server apparatus 300 includes a second display unit 65 to display biological signal data of a patient transmitted from the biological signal hold apparatus 100 and a printer output portion 66 for outputting the displayed biological signal data. Also, in the biological signal monitoring server apparatus 300, a second key input unit 60 is constructed so that a treatment and prescription message can be input to the biological signal hold apparatus 100 according to a monitoring result of receiving biological signal data of a patient displayed in a second display unit 65 and diagnosing the patient using the biological signal data. A second controller 63 receives data applied from the data communicator 64 and stores the received data in a memory unit 61. Also, the second controller 63 controls the second display unit 65 and the printer output portion 66. The biological signal monitoring server apparatus 300 establish a patient control database portion 62 in order to control a number of patients.

Now, the operation of the biological signal monitoring server apparatus 300 which receives the biological signal data of the patient transmitted from the biological signal hold apparatus 100 via the radio communication network, diagnoses the patient using the biological signal data, and transmits a treatment and emergency prescription message to the biological signal hold apparatus 100, will be described in more detail.

If the biological signal hold apparatus 100 is connected to the data communicator 64 via the radio communication network to enable data communication, the alarm generator 67 generates an alarm notifying that the former is connected to the latter, which enables a monitoring personnel such as a doctor or a nurse to recognize the alarm. The second controller 63 instructs the memory unit 61 to store the biological signal data indicating an abnormality of a patient received via the data communicator 64, and outputs a control signal to be displayed in the second display unit 65. The monitoring personnel monitors the biological signal data of the patient displayed in the second display unit 65 and inputs a treatment and emergency prescription message via the second key input unit 60. Also, the monitoring personnel operates the second key input unit 60 so that the input message is displayed in the second display unit 65. The second controller 63 receives the input message and outputs a control signal for allowing the input message to be transmitted to the radio modem 40 in the biological signal hold apparatus 100 attached to the patient via the data communicator 64. Also, the second controller 63 outputs a control signal to the printer output portion 66 to print the biological signal data displayed in the second display unit 65. Also, the second controller 63 outputs a control signal to the patient control database portion 62 to control a number of patients, and reads and displays the stored patient records if necessary.

As described above, the present invention can monitor patients using biological signals, for example, an electrocardiogram, a blood pressure, a brain wave, a blood sugar, which are generated from each organ of the human body, and can see where a patient in an emergency situation is using a global positioning system (GPS) of a satellite.

Thus, the present invention provides a real-time biological signal monitoring system using a radio communication network in which biological signal data is checked using a portable biological signal hold apparatus, the checked data is transmitted to a monitoring center via an aerial radio communication network when it is judged as abnormality, and then the monitoring center transmits diagnosis and prescription information to the biological signal hold apparatus in response thereto. Accordingly, the present invention provides an effect capable of monitoring and providing an emergency treatment on a real-time basis in a remote monitoring center. Also, the present invention transmits a signal to a monitoring center only when it is judged as the occurrence of an abnormality without using an expensive storage unit, which can allow a chronic patient to be monitored ordinarily, resulting in providing a more economical apparatus compared with the conventional biological signal remote measuring apparatus.

INDUSTRIAL APPLICABILITY

The present invention can be used in a portable medical apparatus for measuring biological signal data of a patient, diagnosing, prescribing and treating illness of the patient according to the measured biological signal data. Also, the present invention can be used to check where a patient is positioned using a GPS.

What is claimed is:

1. A real-time biological signal monitoring system using a radio communication network comprising:

a portable biological signal hold apparatus (100) adapted to be attached to the body of a patient for measuring biological signal data, judging whether or not the measured biological signal data indicates a normal condition of the body, and transmitting biological signal data indicating an abnormality via the radio communication network whenever it is judged as an abnormal state;

a biological signal monitoring server apparatus (300) for diagnosing the biological signal data with which an abnormality is recognized from the biological signal hold apparatus (100) via the radio communication network and transmitting a resultant prescription message to the biological signal hold apparatus (100); and a relay station (200) for playing a role of relaying abnormal biological signal data transmitted from the biological signal hold apparatus (100) to the biological signal monitoring server apparatus (300) in a hospital.

2. The real-time biological signal monitoring system using the radio communication network according to claim 1, wherein said portable biological signal hold apparatus (100) comprises:

a biological signal data measuring unit (20) attached to the body of the patient for sensing a minute electrical signal generated during the activity of each organ of the body to display the sensed electrical signal into biological signal data;

a biological signal data analysis unit (30) for storing biological signal data indicating a normality in advance, and diagnosing an abnormality using the biological signal data applied from said biological signal data measuring unit (20) on the basis of the normal biological signal data;

a radio modem (40) connected to said radio communication network for transmitting the biological signal data to said biological signal monitoring server apparatus (300) if said biological signal analysis unit (30) finds out biological signal data indicating an abnormality; and a display unit (50) for displaying a prescription message transmitted from said biological signal monitoring server apparatus (300).

3. The real-time biological signal monitoring system using the radio communication network according to claim 2, wherein said portable biological signal hold apparatus (100) further comprises a first key input unit (10) which can manually input a signal indicating an abnormality to said biological signal monitoring server apparatus.

4. The real-time biological signal monitoring system using the radio communication network according to claim 2, wherein said biological signal data measuring unit (20) comprises:

electrode means (21) having a predetermined number of electrodes each of which is attached to the body of the patient, for sensing an electrical signal of the body;

an analog signal processor (23) for amplifying the electrical signal sensed in said electrode means (21) and processing the amplified signal;

an analog-to-digital converter (25) for converting the analog signal processed biological signal data into a digital signal; and a digital signal processor (27) for processing the digital converted biological signal data and outputting the processed data to said biological signal data analysis unit (30).

5. The real-time biological signal monitoring system using the radio communication network according to claim 2, wherein said biological signal data analysis (30) unit comprises:

a first controller (35) which stores biological signal data indicating a normality in advance, receives the measured biological signal data from said biological signal data measuring unit, checks whether the received biological signal data indicates an abnormality based on the prestored biological signal data, and outputs a control signal to said radio modem (40) to perform a radio communication whenever the biological signal data indicates the abnormality; and a main memory (31) for temporarily storing as a many biological signal data as several minutes preceding or following the biological signal data indicating the abnormality, for a predetermined length of time.

6. The real-time biological signal monitoring system using the radio communication network according to claim 5, wherein said biological signal data analysis unit (30)

further comprises an auxiliary memory (33) for storing the biological signal data for a long time.

7. The real-time biological signal monitoring system using the radio communication network according to claim 1, wherein said biological signal monitoring server apparatus (300) comprises:

a data communication portion (64) connected to said biological signal hold apparatus (100) via the radio communication network to enable data transmission and reception;

a second display unit (65) for displaying the abnormality using the biological signal data received via said data communication portion (64);

a second key input unit (60) for inputting a prescription message corresponding to a diagnostic result obtained by monitoring the biological signal data indicating the abnormality displayed in said second display unit (65) and diagnosing the state of the patient;

a memory unit (61) for storing received biological signal data indicating the abnormality which is transmitted via said data communication portion (64); and a second controller (63) for outputting a radio communication control signal to said data communication portion (64), in order to transmit the prescription message to said biological signal hold apparatus (100).

8. The real-time biological signal monitoring system using the radio communication network according to claim 7, further comprising an alarm generator (67) for generating an alarm whenever the biological signal data received from said data communication portion (64) is applied thereto.

9. The real-time biological signal monitoring system using the radio communication network according to claim 7, further comprising a printer output portion (66) for printing the biological signal data indicating the abnormality displayed in said second display unit (65).

10. The real-time biological signal monitoring system using the radio communication network according to claim 7, further comprising a patient control database portion (62) for collecting the biological signal data of each patient stored in said memory unit (61) and controlling biological signal data with respect to a number of patients.

11. A real-time biological signal monitoring system using the radio communication network according to claim 1, comprising, in combination, said portable biological signal hold apparatus (100), biological signal monitoring server apparatus (300), relay station (200) and radio communication network.

12. A real-time biological signal monitoring system using a radio communication network comprising:

a portable biological signal hold apparatus (100) adapted to be attached to the body of a patient for measuring biological signal data, judging whether or not the measured biological signal indicates a normal condition of the body, and transmitting biological signal data indicating an abnormality via the radio communication network whenever it is judged as an abnormal state;

a biological signal monitoring server apparatus (300) for diagnosing the biological signal data with which an abnormality is recognized from the biological signal hold apparatus (100) via the radio communication network and transmitting a resultant prescription message to the biological signal hold apparatus (100); and a relay station (200) for playing a role of relaying abnormal biological signal data transmitted from the biological signal hold apparatus (100) to the biological signal monitoring server apparatus (300) in a hospital; wherein said portable biological hold apparatus (100) comprises, in a single unit:

a biological signal data measuring unit (20) attached to the body of the patient for sensing a minute electrical signal generated during the activity of each organ of the body to display the sensed electrical signal into biological signal data;

a biological signal data analysis unit (30) for storing biological signal data indicating a normality in advance, and diagnosing an abnormality using the biological signal data applied from said biological signal data measuring unit (20) on the basis of the normal biological signal data;

a radio modem (40) connected to said radio communication network for transmitting the biological signal data to said biological signal monitoring server apparatus (300) if said biological signal analysis unit (30) finds out biological signal data indicating an abnormality; and a display unit (50) for displaying a prescription message transmitted from said biological signal monitoring server apparatus (300).

13. The real-time biological signal monitoring system using the radio communication network according to claim 12, wherein said portable biological signal hold apparatus (100) further comprises, in said single unit, a first key input unit (10) which can manually input a signal indicating an abnormality to said biological signal monitoring server apparatus (300).

* * * * *